US009924950B2

(12) United States Patent
Couture et al.

(10) Patent No.: US 9,924,950 B2
(45) Date of Patent: Mar. 27, 2018

(54) PATIENT SPECIFIC INSTRUMENTATION (PSI) FOR ORTHOPEDIC SURGERY AND SYSTEMS AND METHODS FOR USING X-RAYS TO PRODUCE SAME

(71) Applicant: Zimmer Inc, Warsaw, IN (US)

(72) Inventors: Pierre Couture, Montreal (CA); Trong Tin Nguyen, Laval (CA); Anselm Jakob Neurohr, Montreal (CA); Jean-Sébastien Mérette, Mont-St-Hilaire (CA)

(73) Assignee: ZIMMER, INC., Warsaw, IN (US)

( * ) Notice: Subject to any disclaimer, the term of this patent is extended or adjusted under 35 U.S.C. 154(b) by 653 days.

(21) Appl. No.: 14/496,924

(22) Filed: Sep. 25, 2014

(65) Prior Publication Data

US 2016/0089153 A1 Mar. 31, 2016

Related U.S. Application Data

(60) Provisional application No. 61/882,410, filed on Sep. 25, 2013.

(51) Int. Cl.
*A61B 17/15* (2006.01)
*A61B 17/17* (2006.01)
(Continued)

(52) U.S. Cl.
CPC .......... *A61B 17/154* (2013.01); *A61B 17/155* (2013.01); *A61B 17/157* (2013.01);
(Continued)

(58) Field of Classification Search
CPC ..... A61B 17/15; A61B 17/151; A61B 17/155; A61B 17/157; A61B 17/1764
(Continued)

(56) References Cited

U.S. PATENT DOCUMENTS 4,841,975 A * 6/1989 Woolson .............. A61B 17/154
378/205
5,098,383 A 3/1992 Hemmy et al.
(Continued)

FOREIGN PATENT DOCUMENTS

AU 2004293091 A1 6/2005
AU 2004293104 A1 6/2005
(Continued)

OTHER PUBLICATIONS

Taylor et al, "Computer-Integrated Surgery, Technology and Clinical Applications", The MIT Press, Cambridge, MA, London, UK, pp. 451-463.
(Continued)

*Primary Examiner* — Eric S Gibson
(74) *Attorney, Agent, or Firm* — Norton Rose Fulbright

(57) ABSTRACT

A method of creating a patient specific instrument (PSI) for use in knee replacement surgery is described which includes performing at least two X-ray scans of a bone, each of the X-ray scans being taken from different angular positions, generating a digital bone model of the bone based solely on the X-ray scans, planning the PSI based on the digital bone model, including determining locations for one or more anchor points on the PSI which are adapted to abut a surface of the bone, the determined locations of the anchor points being disposed on the PSI at locations corresponding to areas of expected high accuracy on the digital bone model generated by the X-ray scans. The areas of expected high accuracy include at least a peripheral bone contour in at least one of the angular position of the X-ray scans. A suite of such PSI instruments is also described.

9 Claims, 13 Drawing Sheets

(51) Int. Cl.
  *G06F 19/00* (2018.01)
  *A61B 34/10* (2016.01)
  *A61B 17/56* (2006.01)

(52) U.S. Cl.
  CPC .......... *A61B 17/1764* (2013.01); *A61B 34/10* (2016.02); *G06F 19/3437* (2013.01); *A61B 2017/568* (2013.01); *A61B 2034/108* (2016.02)

(58) Field of Classification Search
  USPC ................................................ 606/86 R–89
  See application file for complete search history.

(56) References Cited

U.S. PATENT DOCUMENTS

| | | | |
|---|---|---|---|
| 5,490,854 A | | 2/1996 | Fisher et al. |
| 5,682,886 A | * | 11/1997 | Delp .................. A61B 17/154 |
| | | | 128/920 |
| 5,768,134 A | | 6/1998 | Swaelens et al. |
| 5,871,018 A | | 2/1999 | Delp et al. |
| 5,916,219 A | | 6/1999 | Matsuno et al. |
| 5,916,220 A | * | 6/1999 | Masini ................. A61B 17/155 |
| | | | 606/87 |
| 2,090,114 A | | 7/2000 | Matsuno et al. |
| 6,090,114 A | | 7/2000 | Matsuno et al. |
| 6,701,174 B1 | | 3/2004 | Krause et al. |
| 7,357,057 B2 | | 4/2008 | Chiang |
| 7,468,075 B2 | | 12/2008 | Lang et al. |
| 7,510,557 B1 | | 3/2009 | Bonutti |
| 7,534,263 B2 | | 5/2009 | Burdulis |
| 7,618,451 B2 | | 11/2009 | Berez et al. |
| 7,634,119 B2 | | 12/2009 | Tsougarakis et al. |
| 7,717,956 B2 | | 5/2010 | Lang |
| 7,796,791 B2 | | 9/2010 | Tsougarakis et al. |
| 7,799,077 B2 | | 9/2010 | Lang et al. |
| 7,806,896 B1 | | 10/2010 | Bonutti |
| 7,806,897 B1 | | 10/2010 | Bonutti |
| 7,837,621 B2 | | 11/2010 | Krause et al. |
| 7,967,868 B2 | | 6/2011 | White et al. |
| 7,981,158 B2 | | 7/2011 | Fitz et al. |
| 8,062,302 B2 | | 11/2011 | Lang et al. |
| 8,066,708 B2 | | 11/2011 | Lang et al. |
| 8,070,752 B2 | | 12/2011 | Metzger et al. |
| 8,077,950 B2 | | 12/2011 | Tsougarakis et al. |
| 8,083,745 B2 | | 12/2011 | Lang et al. |
| 8,092,465 B2 | | 1/2012 | Metzger et al. |
| 8,094,900 B2 | | 1/2012 | Steines et al. |
| 8,105,330 B2 | | 1/2012 | Fitz et al. |
| 8,122,582 B2 | | 2/2012 | Burdulis, Jr. et al. |
| 8,133,234 B2 | | 3/2012 | Meridew et al. |
| 8,160,345 B2 | | 4/2012 | Pavlovskaia et al. |
| 8,175,683 B2 | | 5/2012 | Roose |
| 8,221,430 B2 | | 7/2012 | Park et al. |
| 8,234,097 B2 | | 7/2012 | Steines et al. |
| 8,241,293 B2 | | 8/2012 | Stone et al. |
| 8,265,790 B2 | * | 9/2012 | Amiot .................... G01C 21/16 |
| | | | 606/130 |
| 8,282,646 B2 | | 10/2012 | Schoenefeld et al. |
| 8,298,237 B2 | | 10/2012 | Schoenefeld |
| 8,337,501 B2 | | 12/2012 | Fitz et al. |
| 8,337,507 B2 | | 12/2012 | Lang et al. |
| 8,343,218 B2 | | 1/2013 | Lang et al. |
| 8,366,771 B2 | | 2/2013 | Burdulis et al. |
| 8,377,129 B2 | | 2/2013 | Fitz et al. |
| 8,439,926 B2 | | 5/2013 | Bojarski et al. |
| 8,460,304 B2 | | 6/2013 | Fitz et al. |
| 8,480,754 B2 | | 7/2013 | Bojarski et al. |
| 8,500,740 B2 | | 8/2013 | Bojarski et al. |
| 8,529,568 B2 | | 9/2013 | Bouadi |
| 8,529,630 B2 | | 9/2013 | Bojarski |
| 8,545,569 B2 | | 9/2013 | Fitz et al. |
| 8,545,569 B2 | | 10/2013 | Fitz et al. |
| 8,551,099 B2 | | 10/2013 | Lang |
| 8,551,102 B2 | | 10/2013 | Fitz et al. |
| 8,551,103 B2 | | 10/2013 | Fitz et al. |
| 8,551,108 B2 | * | 10/2013 | Pelletier ................. A61B 34/20 |
| | | | 606/102 |
| 8,551,169 B2 | | 10/2013 | Fitz et al. |
| 8,556,906 B2 | | 10/2013 | Fitz et al. |
| 8,556,907 B2 | | 10/2013 | Fitz et al. |
| 8,556,971 B2 | | 10/2013 | Lang |
| 8,556,983 B2 | | 10/2013 | Bojarski et al. |
| 8,561,278 B2 | | 10/2013 | Fitz et al. |
| 8,562,611 B2 | | 10/2013 | Fitz et al. |
| 8,562,618 B2 | | 10/2013 | Fitz et al. |
| 8,568,479 B2 | | 10/2013 | Fitz et al. |
| 8,568,480 B2 | | 10/2013 | Fitz et al. |
| 8,617,172 B2 | | 12/2013 | Fitz et al. |
| 8,617,242 B2 | | 12/2013 | Philipp |
| 8,623,026 B2 | | 1/2014 | Wong et al. |
| 8,634,617 B2 | | 1/2014 | Tsougarakis et al. |
| 8,638,998 B2 | | 1/2014 | Steines et al. |
| 8,641,716 B2 | | 2/2014 | Fitz et al. |
| 8,657,827 B2 | | 2/2014 | Fitz et al. |
| 8,682,052 B2 | | 3/2014 | Fitz et al. |
| 9,314,251 B2 | * | 4/2016 | Aram .................. A61B 17/157 |
| 9,532,845 B1 | * | 1/2017 | Dossett ................ A61B 19/50 |
| 2003/0055502 A1 | | 3/2003 | Lang et al. |
| 2003/0216669 A1 | | 11/2003 | Lang et al. |
| 2004/0068187 A1 | | 4/2004 | Krause et al. |
| 2004/0133276 A1 | | 7/2004 | Lang et al. |
| 2004/0138754 A1 | | 7/2004 | Lang et al. |
| 2004/0147927 A1 | | 7/2004 | Tsougarakis et al. |
| 2004/0153079 A1 | | 8/2004 | Tsougarakis et al. |
| 2004/0204644 A1 | | 10/2004 | Tsougarakis et al. |
| 2004/0204760 A1 | | 10/2004 | Fitz et al. |
| 2004/0236424 A1 | | 11/2004 | Berez et al. |
| 2005/0234461 A1 | | 10/2005 | Burdulis et al. |
| 2005/0267584 A1 | | 12/2005 | Burdulis et al. |
| 2006/0111722 A1 | | 5/2006 | Bouadi |
| 2007/0016209 A1 | * | 1/2007 | Ammann ............... A61B 17/15 |
| | | | 606/79 |
| 2007/0083266 A1 | | 4/2007 | Lang |
| 2007/0100462 A1 | | 5/2007 | Lang et al. |
| 2007/0156171 A1 | | 7/2007 | Lang et al. |
| 2007/0157783 A1 | | 7/2007 | Chiang |
| 2007/0173850 A1 | * | 7/2007 | Rangaiah ............. A61B 17/154 |
| | | | 606/87 |
| 2007/0198022 A1 | | 8/2007 | Lang et al. |
| 2007/0226986 A1 | | 10/2007 | Park et al. |
| 2007/0233141 A1 | * | 10/2007 | Park ..................... A61B 17/155 |
| | | | 606/88 |
| 2007/0233269 A1 | | 10/2007 | Steines et al. |
| 2007/0244487 A1 | * | 10/2007 | Ammann ............... A61B 17/15 |
| | | | 606/88 |
| 2007/0250169 A1 | | 10/2007 | Lang |
| 2008/0114370 A1 | | 5/2008 | Schoenefeld |
| 2008/0147072 A1 | * | 6/2008 | Park ...................... A61B 17/17 |
| | | | 606/87 |
| 2008/0161815 A1 | * | 7/2008 | Schoenefeld ........ A61B 17/154 |
| | | | 606/87 |
| 2008/0195109 A1 | * | 8/2008 | Hunter .................. A61B 17/155 |
| | | | 606/87 |
| 2008/0195216 A1 | | 8/2008 | Philipp |
| 2008/0208199 A1 | * | 8/2008 | Ammann ............... A61B 17/15 |
| | | | 606/88 |
| 2008/0243127 A1 | | 10/2008 | Lang et al. |
| 2008/0262624 A1 | * | 10/2008 | White ................... A61B 17/154 |
| | | | 623/20.32 |
| 2008/0275452 A1 | | 11/2008 | Lang et al. |
| 2008/0281328 A1 | | 11/2008 | Lang et al. |
| 2008/0281329 A1 | | 11/2008 | Fitz et al. |
| 2008/0281426 A1 | | 11/2008 | Fitz et al. |
| 2008/0287954 A1 | * | 11/2008 | Kunz .................... A61B 17/175 |
| | | | 606/87 |
| 2008/0319491 A1 | * | 12/2008 | Schoenefeld .......... A61B 17/15 |
| | | | 606/86 R |
| 2009/0024131 A1 | | 1/2009 | Metzgu et al. |
| 2009/0088753 A1 | | 4/2009 | Aram et al. |
| 2009/0088754 A1 | | 4/2009 | Aker et al. |
| 2009/0088755 A1 | | 4/2009 | Aker et al. |
| 2009/0088758 A1 | * | 4/2009 | Bennett ................ A61B 17/155 |
| | | | 606/82 |

(56) References Cited

U.S. PATENT DOCUMENTS

| | | | |
|---|---|---|---|
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1* | 5/2009 | Park | A61B 5/055 606/88 |
| 2009/0157083 A1* | 6/2009 | Park | A61B 5/055 606/88 |
| 2009/0222014 A1* | 9/2009 | Bojarski | A61B 17/155 606/88 |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0270868 A1* | 10/2009 | Park | A61B 17/15 606/87 |
| 2009/0276045 A1 | 11/2009 | Lang | |
| 2009/0306676 A1 | 12/2009 | Lang et al. | |
| 2009/0307893 A1 | 12/2009 | Burdulis, Jr. et al. | |
| 2009/0312805 A1 | 12/2009 | Lang et al. | |
| 2010/0023015 A1* | 1/2010 | Park | A61B 17/15 606/87 |
| 2010/0042105 A1 | 2/2010 | Park et al. | |
| 2010/0049195 A1 | 2/2010 | Park et al. | |
| 2010/0054572 A1 | 3/2010 | Tsougarakis et al. | |
| 2010/0076563 A1* | 3/2010 | Otto | A61B 5/103 623/20.14 |
| 2010/0082035 A1 | 4/2010 | Keefer | |
| 2010/0087829 A1* | 4/2010 | Metzger | A61B 17/15 606/96 |
| 2010/0152741 A1* | 6/2010 | Park | A61B 17/155 606/89 |
| 2010/0152782 A1 | 6/2010 | Stone et al. | |
| 2010/0160917 A1 | 6/2010 | Fitz et al. | |
| 2010/0168754 A1 | 7/2010 | Fitz et al. | |
| 2010/0174376 A1 | 7/2010 | Lang et al. | |
| 2010/0185202 A1 | 7/2010 | Lester et al. | |
| 2010/0191244 A1 | 7/2010 | White et al. | |
| 2010/0212138 A1* | 8/2010 | Carroll | A61B 17/155 29/446 |
| 2010/0217270 A1 | 8/2010 | Polinski et al. | |
| 2010/0217338 A1 | 8/2010 | Carroll et al. | |
| 2010/0228257 A1* | 9/2010 | Bonutti | A61B 17/025 606/87 |
| 2010/0234849 A1 | 9/2010 | Bouadi | |
| 2010/0256479 A1* | 10/2010 | Park | A61B 5/055 600/410 |
| 2010/0262150 A1 | 10/2010 | Lian | |
| 2010/0274534 A1 | 10/2010 | Steines et al. | |
| 2010/0281678 A1 | 11/2010 | Burdulis, Jr. et al. | |
| 2010/0286700 A1 | 11/2010 | Snider et al. | |
| 2010/0298894 A1 | 11/2010 | Bojarski et al. | |
| 2010/0303313 A1 | 12/2010 | Lang et al. | |
| 2010/0303317 A1 | 12/2010 | Tsougarakis et al. | |
| 2010/0303324 A1 | 12/2010 | Lang et al. | |
| 2010/0305573 A1 | 12/2010 | Fitz et al. | |
| 2010/0305574 A1 | 12/2010 | Fitz et al. | |
| 2010/0305708 A1 | 12/2010 | Lang et al. | |
| 2010/0305907 A1 | 12/2010 | Fitz et al. | |
| 2010/0329530 A1 | 12/2010 | Lang et al. | |
| 2011/0015636 A1* | 1/2011 | Katrana | A61B 17/15 606/87 |
| 2011/0015637 A1 | 1/2011 | De Smedt et al. | |
| 2011/0015639 A1 | 1/2011 | Metzger et al. | |
| 2011/0029091 A1 | 2/2011 | Bojarski et al. | |
| 2011/0029093 A1 | 2/2011 | Bojarski et al. | |
| 2011/0040168 A1 | 2/2011 | Arnaud et al. | |
| 2011/0054478 A1 | 3/2011 | Vanasse et al. | |
| 2011/0060341 A1* | 3/2011 | Angibaud | A61B 17/155 606/89 |
| 2011/0066193 A1 | 3/2011 | Lang et al. | |
| 2011/0066245 A1 | 3/2011 | Lang et al. | |
| 2011/0071533 A1* | 3/2011 | Metzger | A61B 17/157 606/88 |
| 2011/0071581 A1 | 3/2011 | Lang et al. | |
| 2011/0071645 A1 | 3/2011 | Bojarski et al. | |
| 2011/0071802 A1 | 3/2011 | Bojarski et al. | |
| 2011/0087332 A1 | 4/2011 | Bojarski et al. | |
| 2011/0092977 A1* | 4/2011 | Salehi | A61B 17/155 606/88 |
| 2011/0093023 A1* | 4/2011 | Lee | A61B 17/175 606/86 R |
| 2011/0093108 A1* | 4/2011 | Ashby | A61B 34/10 700/103 |
| 2011/0106093 A1 | 5/2011 | Romano et al. | |
| 2011/0130761 A1* | 6/2011 | Plaskos | A61B 17/155 606/87 |
| 2011/0144760 A1 | 6/2011 | Wong et al. | |
| 2011/0160736 A1 | 6/2011 | Meridew et al. | |
| 2011/0160867 A1 | 6/2011 | Meridew et al. | |
| 2011/0166578 A1* | 7/2011 | Stone | A61B 17/151 606/88 |
| 2011/0172672 A1* | 7/2011 | Dubeau | A61B 17/151 606/87 |
| 2011/0184419 A1 | 7/2011 | Meridew et al. | |
| 2011/0196377 A1 | 8/2011 | Hodorek et al. | |
| 2011/0213368 A1 | 9/2011 | Fitz et al. | |
| 2011/0213373 A1 | 9/2011 | Fitz et al. | |
| 2011/0213374 A1 | 9/2011 | Fitz et al. | |
| 2011/0213376 A1 | 9/2011 | Maxson et al. | |
| 2011/0213377 A1 | 9/2011 | Lang et al. | |
| 2011/0213427 A1 | 9/2011 | Fitz et al. | |
| 2011/0213428 A1 | 9/2011 | Fitz et al. | |
| 2011/0213429 A1 | 9/2011 | Lang et al. | |
| 2011/0213430 A1 | 9/2011 | Lang et al. | |
| 2011/0213431 A1 | 9/2011 | Fitz et al. | |
| 2011/0214279 A1 | 9/2011 | Park et al. | |
| 2011/0218458 A1* | 9/2011 | Valin | A61B 34/20 600/595 |
| 2011/0218539 A1 | 9/2011 | Fitz et al. | |
| 2011/0218545 A1* | 9/2011 | Catanzarite | A61B 17/155 606/96 |
| 2011/0218584 A1 | 9/2011 | Fitz et al. | |
| 2011/0224674 A1 | 9/2011 | White et al. | |
| 2011/0230888 A1 | 9/2011 | Lang et al. | |
| 2011/0238073 A1 | 9/2011 | Lang et al. | |
| 2011/0245835 A1* | 10/2011 | Dodds | A61B 17/155 606/87 |
| 2011/0266265 A1 | 11/2011 | Lang | |
| 2011/0295329 A1 | 12/2011 | Fitz et al. | |
| 2011/0295378 A1 | 12/2011 | Bojarski et al. | |
| 2011/0313423 A1 | 12/2011 | Lang et al. | |
| 2011/0313424 A1 | 12/2011 | Bono et al. | |
| 2011/0319897 A1 | 12/2011 | Lang et al. | |
| 2011/0319900 A1 | 12/2011 | Lang et al. | |
| 2012/0010711 A1 | 1/2012 | Antonyshyn et al. | |
| 2012/0029520 A1 | 2/2012 | Lang et al. | |
| 2012/0041445 A1 | 2/2012 | Roose et al. | |
| 2012/0041446 A1* | 2/2012 | Wong | A61B 17/1703 606/96 |
| 2012/0065640 A1* | 3/2012 | Metzger | A61B 17/154 606/88 |
| 2012/0066892 A1 | 3/2012 | Lang et al. | |
| 2012/0071881 A1 | 3/2012 | Lang et al. | |
| 2012/0071882 A1 | 3/2012 | Lang et al. | |
| 2012/0071883 A1 | 3/2012 | Lang et al. | |
| 2012/0072185 A1 | 3/2012 | Lang et al. | |
| 2012/0078254 A1* | 3/2012 | Ashby | A61B 17/1764 606/79 |
| 2012/0078258 A1 | 3/2012 | Lo et al. | |
| 2012/0078259 A1 | 3/2012 | Meridew | |
| 2012/0093377 A1 | 4/2012 | Tsougarakis et al. | |
| 2012/0101503 A1 | 4/2012 | Lang et al. | |
| 2012/0109138 A1 | 5/2012 | Meridew et al. | |
| 2012/0116203 A1 | 5/2012 | Vancraen et al. | |

(56) References Cited

U.S. PATENT DOCUMENTS

| | | | |
|---|---|---|---|
| 2012/0116562 A1* | 5/2012 | Agnihotri | A61B 17/155 700/98 |
| 2012/0123422 A1 | 5/2012 | Agnihotri et al. | |
| 2012/0123423 A1 | 5/2012 | Fryman | |
| 2012/0130382 A1 | 5/2012 | Iannotti et al. | |
| 2012/0130687 A1 | 5/2012 | Otto et al. | |
| 2012/0141034 A1 | 6/2012 | Iannotti et al. | |
| 2012/0143197 A1 | 6/2012 | Lang et al. | |
| 2012/0143198 A1* | 6/2012 | Boyer | A61B 17/151 606/87 |
| 2012/0151730 A1 | 6/2012 | Fitz et al. | |
| 2012/0158001 A1 | 6/2012 | Burdulis, Jr. et al. | |
| 2012/0165820 A1 | 6/2012 | De Smedt et al. | |
| 2012/0172884 A1 | 7/2012 | Zheng et al. | |
| 2012/0179147 A1* | 7/2012 | Geebelen | A61B 17/17 606/1 |
| 2012/0191205 A1 | 7/2012 | Bojarski et al. | |
| 2012/0191420 A1 | 7/2012 | Bojarski et al. | |
| 2012/0192401 A1* | 8/2012 | Pavlovskaia | G06K 9/48 29/428 |
| 2012/0197260 A1 | 8/2012 | Fitz et al. | |
| 2012/0197408 A1 | 8/2012 | Lang et al. | |
| 2012/0201440 A1 | 8/2012 | Steines et al. | |
| 2012/0203233 A1* | 8/2012 | Yoshida | A61B 17/154 606/87 |
| 2012/0209276 A1 | 8/2012 | Schuster | |
| 2012/0209394 A1 | 8/2012 | Bojarski et al. | |
| 2012/0215226 A1 | 8/2012 | Bonutti | |
| 2012/0221008 A1 | 8/2012 | Carroll et al. | |
| 2012/0226283 A1 | 9/2012 | Meridew et al. | |
| 2012/0232669 A1 | 9/2012 | Bojarski et al. | |
| 2012/0232670 A1 | 9/2012 | Bojarski et al. | |
| 2012/0232671 A1 | 9/2012 | Bojarski | |
| 2012/0239045 A1* | 9/2012 | Li | A61B 17/15 606/88 |
| 2012/0245647 A1 | 9/2012 | Kunz et al. | |
| 2012/0245699 A1 | 9/2012 | Lang et al. | |
| 2012/0265208 A1 | 10/2012 | Smith | |
| 2012/0271366 A1 | 10/2012 | Katrana et al. | |
| 2012/0276509 A1 | 11/2012 | Iannotti et al. | |
| 2012/0277751 A1* | 11/2012 | Catanzarite | A61B 17/155 606/88 |
| 2012/0289966 A1 | 11/2012 | Fitz et al. | |
| 2012/0296337 A1 | 11/2012 | Fitz et al. | |
| 2013/0018379 A1 | 1/2013 | Fitz et al. | |
| 2013/0018380 A1 | 1/2013 | Fitz et al. | |
| 2013/0018464 A1 | 1/2013 | Fitz et al. | |
| 2013/0023884 A1 | 1/2013 | Fitz et al. | |
| 2013/0024000 A1 | 1/2013 | Bojarski et al. | |
| 2013/0030419 A1 | 1/2013 | Fitz et al. | |
| 2013/0030441 A1 | 1/2013 | Fitz et al. | |
| 2013/0060253 A1* | 3/2013 | Couture | A61B 17/155 606/88 |
| 2013/0079781 A1 | 3/2013 | Fitz et al. | |
| 2013/0079876 A1 | 3/2013 | Fitz et al. | |
| 2013/0081247 A1 | 4/2013 | Fitz et al. | |
| 2013/0096562 A1 | 4/2013 | Fitz et al. | |
| 2013/0103363 A1 | 4/2013 | Lang et al. | |
| 2013/0110250 A1 | 5/2013 | Li | |
| 2013/0110471 A1 | 5/2013 | Lang et al. | |
| 2013/0123792 A1 | 5/2013 | Fitz et al. | |
| 2013/0184713 A1 | 7/2013 | Bojarski et al. | |
| 2013/0197870 A1 | 8/2013 | Steines et al. | |
| 2013/0211409 A1 | 8/2013 | Burdulis, Jr. et al. | |
| 2013/0211410 A1 | 8/2013 | Landes et al. | |
| 2013/0211411 A1* | 8/2013 | Tuke | A61B 17/155 606/88 |
| 2013/0211531 A1 | 8/2013 | Steines et al. | |
| 2013/0245803 A1 | 9/2013 | Lang | |
| 2013/0253522 A1 | 9/2013 | Bojarski et al. | |
| 2013/0289570 A1 | 10/2013 | Chao | |
| 2013/0296865 A1* | 11/2013 | Aram | A61B 17/1764 606/80 |
| 2013/0296874 A1 | 11/2013 | Chao | |
| 2013/0297031 A1 | 11/2013 | Hafez | |
| 2013/0310836 A1* | 11/2013 | Raub | A61B 17/155 606/84 |
| 2013/0317511 A1 | 11/2013 | Bojarski et al. | |
| 2013/0331850 A1 | 12/2013 | Bojarski et al. | |
| 2014/0005792 A1 | 1/2014 | Lang et al. | |
| 2014/0029814 A1 | 1/2014 | Fitz et al. | |
| 2014/0031672 A1* | 1/2014 | McCaulley | A61B 5/06 600/424 |
| 2014/0031826 A1 | 1/2014 | Bojarski et al. | |
| 2014/0039631 A1 | 2/2014 | Bojarski et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0086780 A1 | 3/2014 | Miller et al. | |
| 2014/0094814 A1* | 4/2014 | Hughes | A61B 17/155 606/88 |
| 2014/0114319 A1* | 4/2014 | Wilkinson | A61B 17/1764 606/88 |
| 2014/0142580 A1* | 5/2014 | Aram | A61B 17/155 606/89 |
| 2015/0032113 A1* | 1/2015 | Anderson | A61B 17/1764 606/88 |
| 2015/0088142 A1* | 3/2015 | Gibson | A61B 17/155 606/88 |
| 2016/0089153 A1* | 3/2016 | Couture | A61B 17/155 606/88 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |

(56) References Cited

FOREIGN PATENT DOCUMENTS

| | | |
|---|---|---|
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008154909 | 12/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |

(56) References Cited

FOREIGN PATENT DOCUMENTS

| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Hofmann et al, "Natural-Knee II System", Intermedics Orthopedics, Austin, TX, 1995.
Extended European Search Report, EP 14846965.3, dated Jun. 8, 2017.

* cited by examiner

PATIENT SPECIFIC INSTRUMENTATION (PSI) FOR ORTHOPEDIC SURGERY AND SYSTEMS AND METHODS FOR USING X-RAYS TO PRODUCE SAME

CROSS-REFERENCE TO RELATED APPLICATIONS

The present application claims priority on U.S. Patent Application No. 61/882,410 filed Sep. 25, 2013, the entire content of which is incorporated herein by reference.

TECHNICAL FIELD

The present disclosure relates generally to patient specific instrumentation (PSI) used in orthopedic surgical applications, and more particularly to PSI devices and/or implants which are created based on patient specific bone models produced from X-rays.

BACKGROUND

Improvements in the design, creation and use of patient specific instrumentation and/or implants (PSI) continue to be sought. PSI devices are purpose designed to suit a specific patient's anatomy. In the context of orthopedic surgical applications, this is most commonly accomplished by first generating a digitized bone model of the specific patient's bone based on images produced from a Magnetic Resonance Imaging (MRI) scan of the patient's anatomy. MRI scans are most often used because they offer precise imaging of the anatomical features of the patient, including bone, cartilage and other soft tissue, which enables the creation of an accurate patient-specific digitized bone model. This bone model can then be used to create PSI devices.

SUMMARY OF THE INVENTION

In accordance with one general aspect of the present invention, there is provided a method of creating a patient specific instrument for use in knee replacement surgery, the method comprising: performing at least two X-ray scans of one or more bones, each of the X-ray scans being taken from different angular positions; generating a digital bone model of said one or more bones based solely on the X-ray scans; planning the patient specific instrument based on the digital bone model, including determining locations for one or more anchor points on the patient specific instrument which are adapted to abut a surface of said one or more bones, the determined locations of the one or more anchor points being disposed on the patient specific instrument corresponding to areas of expected high accuracy on the digital bone model generated by the X-ray scans, said areas of expected high accuracy including at least a peripheral bone contour in at least one of said angular positions; and producing the patient specific instrument having said one or more anchor points thereon.

In accordance with another general aspect of the present invention, there is provided a patient specific instrument for positioning a resection cutting block on a bone during orthopedic knee replacement surgery, the patient specific instrument being formed based on a digital bone model generated solely using at least two X-ray scans taken from different angular positions, the patient specific instrument comprising: a body having a pair of pin guide holes extending therethrough, the pin guide holes adapted to receive bone pins used to fasten the resection cutting block to the bone; and one or more anchor elements on the body adapted to abut one or more surfaces of the bone, the anchor elements being disposed in locations on the body of the patient specific instrument overlying a peripheral bone contour of the bone in at least one of the X-ray scans, said locations and the peripheral bone contour corresponding to areas of expected high accuracy on the digital bone model generated by the two-dimensional X-ray scans.

In accordance with a further general aspect of the present invention, there is provided a method of positioning bone pins for mounting a resection cutting block on a bone during orthopedic knee replacement surgery, including: obtaining at least two X-ray scans of the bone taken from different angular positions, and a digital bone mode of the bone based solely on said X-ray scans; using a patient specific instrument designed based on the digital bone model, the patient specific instrument having one or more anchor points thereon which are adapted to abut a surface of the bone, the anchor points being disposed on the patient specific instrument at locations corresponding to areas of expected high accuracy on the digital bone model generated by the X-ray scans, said areas of expected high accuracy including at least a peripheral bone contour in at least one of said angular positions; engaging the patient specific instrument to the bone by abutting the anchor points against the bone; angularly adjusting the patient specific instrument in at least one of varus-valgus, flexion-extension, and rotation, in order to position the patient specific instrument in a predetermined position and orientation; and inserting the bone pins through corresponding pin holes extending the a body of the patient specific instrument.

BRIEF DESCRIPTION OF THE DRAWINGS

FIG. 13b is a partial perspective anterior-medial view of the PSI femoral pin guide of FIG. 13a.

DETAILED DESCRIPTION

Figure 1:
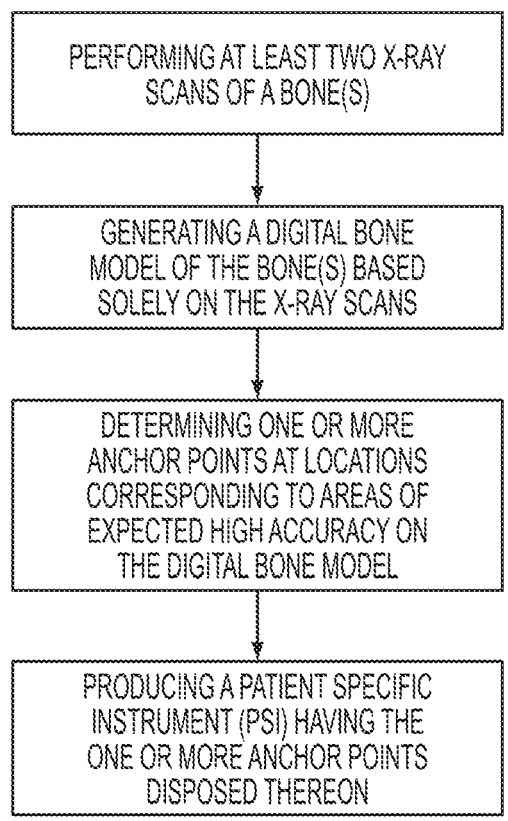
FIG. 1 is a flowchart illustrating a method for forming patient specific instrumentation (PSI) for use in performing total knee replacement (TKR) surgery, in accordance with the present disclosure.

Patient specific instrumentation/instruments/implants (collectively "PSI" as used herein) are purpose designed to suit a specific patient's anatomy, based on a digitized bone model of the anatomy in question. Such PSI devices are most commonly created based on digital bone models that are generated using Magnetic Resonance Imaging (MRI) images of the bone(s) and surrounding soft tissue (e.g. cartilage). MRI scans have to date been largely preferred for the creation of such PSI devices, due to the fact that the MRI scan images are capable of depicting cartilage as well as the bone, thereby ensuring the accuracy of the resulting surgery performed using the PSI device thus produced. However, such MRI scans are both costly and time consuming to conduct.

Accordingly, the present inventors have developed a suite of patient specific surgical implements particularly adapted for use in conducting knee replacement surgery (such as total knee replacement (TKR)), which are specifically designed to be created based on a digital bone model generated only using X-rays taken of the patient's bone(s).

Thus, the presently described system and method enables the creation and use of PSI components for knee surgery which are designed and created using a digital bone model generated using only two-dimensional (2D) X-ray images of the specific patient's bone(s). This enables the PSI components described herein to be created quickly and in a more cost effective manner than with known prior art systems and methods, which require the use of MRI scans to produce the digital bone models.

In accordance with a general aspect of the present disclosure, therefore, a patient specific digital bone model is first created using only X-ray scan images (i.e. no MRI scans are required), so as to digitally reconstruct the bone in a surgical planning computer program and/or a computer assisted surgery (CAS) system. At least two or more X-ray images are required of the patient's bone or bones, which must be taken from different angular positions (e.g. one lateral X-ray and one frontal or anterior X-ray). While one X-ray image may be insufficient, more than two X-ray images may alternately be used. Generally, the greater the number of X-ray scans taken from different angular positions (e.g. lateral, medial, anterior, posterior, etc.), the greater the resulting accuracy of the digital bone model created therefrom. However, the desired accuracy has been found to be obtainable when only two X-rays are taken from perpendicularly disposed angular positions (e.g. lateral and frontal/anterior).

Once a digital bone model is created using the surgical planning computer program and/or CAS system, using only the two or more X-ray images of the bone(s) of the specific patient, a PSI surgical component as described herein is then designed using the CAS system as will be described, and then subsequently created specifically for the patient, using the digital bone model of the patient's anatomy created based only on the X-ray images. The PSI components as described herein may therefore be created, once they have been planned/designed to fit with the digital bone model, out of any suitable material, but these may include plastics or metals which are suitable for use in surgical applications. Ideally, these PSI components are produced rapidly and on site, using an additive manufacturing process such as 3-D printing.

While X-rays are typically perceived as being less precise than MRI images, the present method and system can nevertheless be used to create PSI components which are specially adapted to be formed based on a digitized patient bone model generated using only X-ray images. Thus PSI devices, tool and/or instruments described herein may accordingly be designed and created more time and cost effectively.

As will be seen, because an X-ray generated digital bone model is being used, standard surgical tools, and even previously developed standard patient-specific tools, cannot be readily used. This is because patient specific tools developed based on MRI-generated bone models can be designed knowing precisely where any cartilage and other soft tissue is located. As this is not the case for bone models generated using only X-rays images, any PSI component which is doing to be designed based on such X-ray bone models must be configured in such a way as to maximize the accuracy of the component and more specifically its mounting points with the actual bone, in order to ensure that the end surgical result when this component is used is acceptable.

The presently described PSI components, which are produced based solely on X-ray generated digital bone models, therefore include one or more anchor points thereon that are adapted to abut and/or otherwise engage a surface of the bone and that are disposed on the PSI component at one or more locations corresponding to areas of expected high accuracy on the digital bone model generated by the X-ray scans. These areas of expected high accuracy on the digital bone model will generally correspond to points on a peripheral bone contour in at least one of the angular positions from which an X-ray image is taken. For example, if a frontal, or anterior, X-ray has been taken of the bone, the medial, lateral and proximal outer peripheral contours of the bone will be very accurate in the X-ray image and thus in the resulting digital bone model created thereby. As a result, points on the bone model which are disposed along these medial, lateral and/or proximal peripheral contours of the digital bone model will be areas of expected high accuracy, even if the X-ray image is not capable of revealing any cartilage present. Similarly, if a lateral X-ray has been taken of the bone, the anterior, distal and/or proximal outer peripheral contours of the bone will be very accurate in the X-ray image, and thus in the resulting digital bone model created thereby. As a result, points on the bone model which are substantially disposed along these anterior, distal and proximal outer peripheral contours of the digital bone model will be areas of expected high accuracy, even if the X-ray image is not capable of revealing any cartilage present. Thus, by positioning any anchor or mounting elements of a PSI component in locations on the PSI component which correspond to these areas of expected high accuracy on the X-ray generated bone model, the PSI component so designed is particularly adapted for use without any appreciable loss in accuracy.

The term "anchor", "anchor elements" or "anchor points" as used herein is understood to mean points on the PSI component which engage the bone when the PSI component is mounted thereto, whether this be simply by abutting the bone without being directly fixed thereto (e.g. a bone spike, blade or jack screw which rests on the outer surface of the bone) or by being fastened (e.g. by a pin, bone screw, etc. which penetrates into the bone for rigid fastening thereto). The term "anchor" as used herein therefore does not necessarily imply rigid fastening by penetration of the bone, but rather such anchors fix the PSI component in place on the bone such that relative movement therebetween is not readily possible.

Referring now to the Figures, these general aspects of the present disclosure as outlined above are described and depicted in greater detail with reference to an exemplary orthopedic knee surgery system, and more particularly with respect to performing a total knee replacement (TKR) system involving components and methods specific to both tibia and femur resection and prosthetic reconstruction.

This may include, for example, providing PSI tools and/or implants, formed in order to correspond with the patient specific digital bone model created based on X-ray images. This may further include digitizing the tibial and/or femoral mechanical axis in order to be able to perform the TKR procedure on the patient using the PSI tools. This may be done in conjunction with a CAS system, for example one which employs inertial-based or micro-electro-mechanical sensor (MEMS) trackable members for use in orthopedic surgical applications. The presently described system, surgical tools and methods may therefore be used in conjunction with an inertial-based CAS system employing trackable members having inertial-based sensors, such as the MEMS-based system and method for tracking a reference frame disclosed in United States Patent Application Publication No. US 2011/0218458, and the MEMS-based system and method for planning/guiding alterations to a bone disclosed in U.S. Pat. Nos. 8,265,790 and 8,718,820, and in United States Patent Application Publication No. 2009/0247863, the entire contents of each of which is incorporated herein by reference. However, it is to be understood that the tools and methods described herein may also be used with other CAS systems. The present systems and methods may also be used in conjunction with a tool for digitizing a mechanical axis of a tibia using a CAS system, as described in U.S. Pat. No. 8,551,108, the entire content of which is incorporated herein by reference.

The PSI components of the present disclosure are all particularly adapted for use during orthopedic knee surgery, such as TKR, and as such the surgical components of the present suite of surgical tools will now be described below generally as either tibial or femoral components, respectively adapted for use in the positioning of a resection cutting guide on either the tibia or the femur, for the purposes of preparing the bone for receipt of a prosthetic knee replacement implant. While the actual steps of the TKR surgery are as per those well known by those skilled in the art, the presently described PSI components differ in that they are specifically adapted for use in a system and method which has produced the digital bone model using only X-ray images.

Tibial Components

Figure 4:
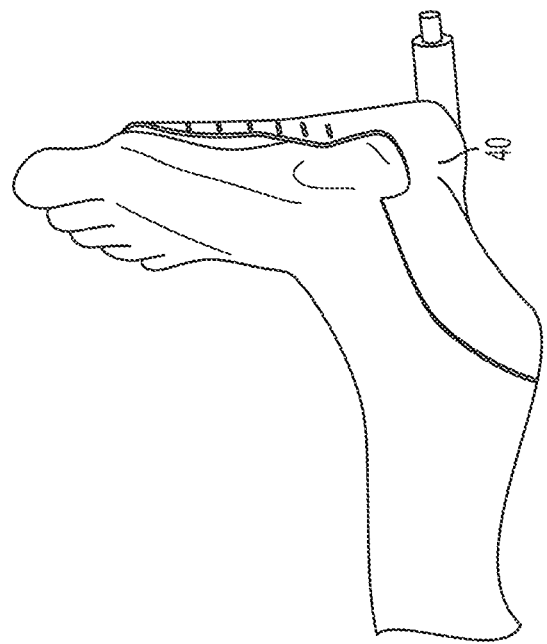
FIG. 4 is a front perspective view of a PSI tibial resection cut guide for use in conjunction with the PSI tibial pin guide of FIG. 2.

In order to be able to resect a proximal end of the tibia T using a resection cutting guide 30, as shown in FIG. 4, locating pins 31 must first be accurately positioned at the desired position and orientation relative to the tibia T, such that the resulting resection cut will be made at the correct position and angle to accept the planned prosthetic tibial implant. Accordingly, several different embodiments will now be presented, each of which can be used to position these locating pins 31.

Figure 2:
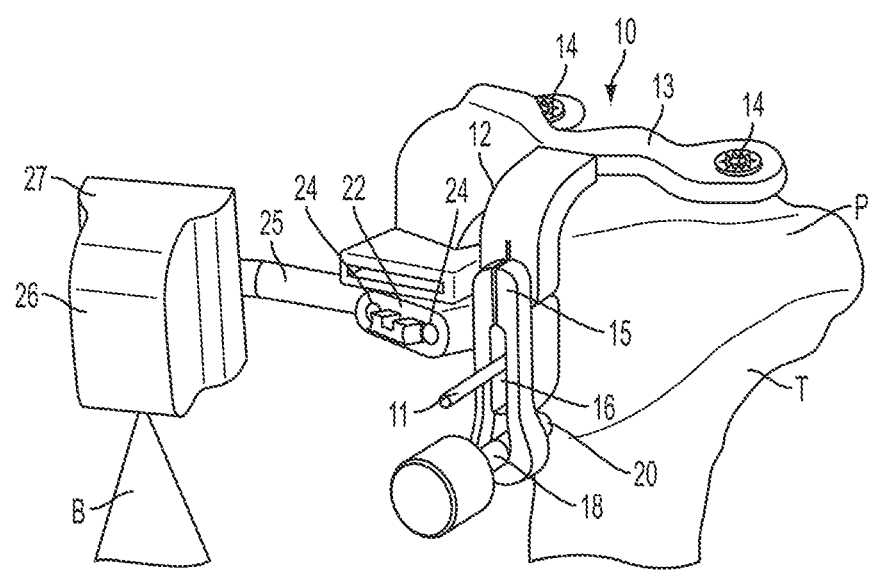
FIG. 2 is front perspective view of a PSI tibial pin guide, produced based on X-rays of the tibia and for use in performing tibial resection during a TKR surgery.
Figure 3:
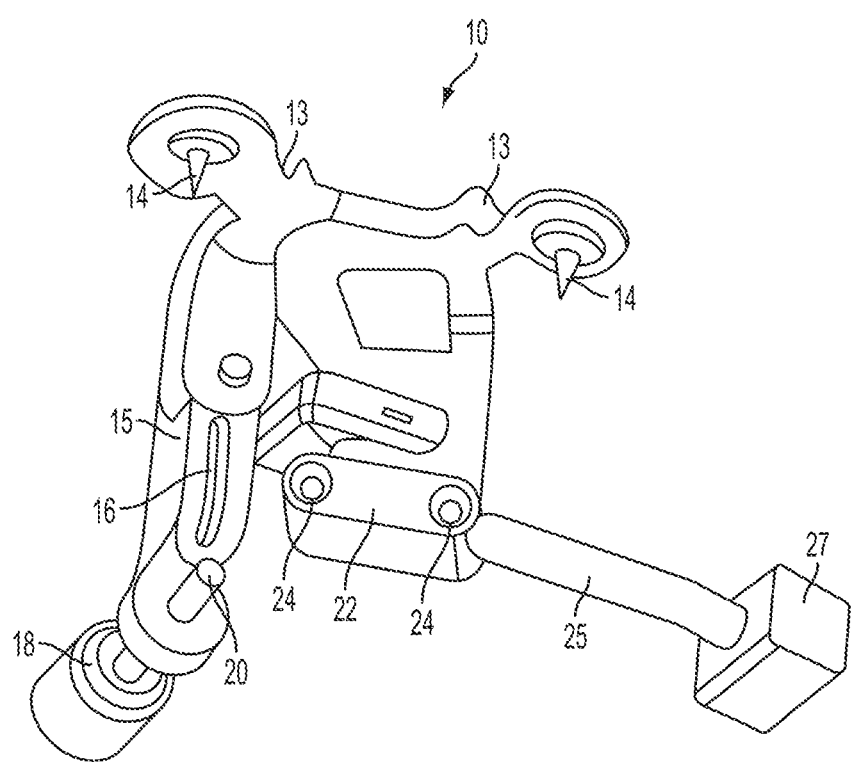
FIG. 3 is a rear perspective view of the PSI tibial pin guide of FIG. 2.

In the embodiment of FIGS. 2-3, a PSI tibial pin guide 10 is shown which is produced based on at least two X-rays of the tibia, taken from two different angular positions as described above. The PSI tibial pin guide 10 includes generally a body 12 including a distally extending portion 15 and a pair of posteriorly extending arms 13. The distally extending portion 15 of the body 12 has a slot 16 formed therein, which extends fully through the distally extending portion 15 and is adapted to receive therethrough an anterior bone pin 11. The slot 16 has a transverse width, in the medial-lateral (M-L) direction, substantially similar although just slightly greater than the diameter of the anterior pin 11. The slot 16 has a length, in the proximal-distal (P-D) direction, that is at least several times the diameter of the anterior pin 11. As such, once the anterior pin is fastened in place in the anterior surface of the tibia T, the PSI tibial pin guide 10 can be mounted thereto by inserting the anterior pin 11 through the slot 16 in the body 12 of the PSI tibial pin guide 10. Given the slot's length, the body 12 of the PSI tibial pin guide 10 can therefore be slid in the P-D direction relative to the fixed anterior pin 11 as required. Although only the anterior pin 11, and not the body 12 of the PSI tibial pin guide 10, is engaged to the bone, this pin-slot engagement nevertheless locates, or constrains, the rotation of the PSI tibial pin guide 10 (i.e. relative to longitudinal axis of the bone) while still permitting angular movement in the Varus-Valgus (V-V) and Flexion-Extension (F-E) orientations/directions.

At an upper end of the body 12 of the PSI tibial pin guide 10, the pair of posteriorly extending arms 13 each have a proximal anchor element 14 disposed near the remote end thereof, the two proximal anchor elements 14 comprising bone spikes or nails. These bone spikes 14 are adapted to penetrate any cartilage on the tibial plateaus P and engage, but not substantially penetrate, the underlying bone surface of the tibial plateau P. These proximal bone anchors 14 accordingly locate, or constrain, the PSI tibial pin guide 10 in the V-V orientation relative thereto.

The remaining angular constraint required, and for which adjustment is provided, for the PSI tibial pin guide 10 is in the F-E direction. Accordingly, the PSI tibial pin guide 10 includes an adjustment jack screw 18 disposed at a remote end of the distally extending portion 15 of the body 12, which has a bone abutting tip 20 thereon that forms another anchor point or anchor element for abutting the tibia T. By rotating the jack screw 18, the position of the body 12 of the PSI tibial pin guide 10 relative to the tibia T can be adjusted in the F-E direction/orientation.

Accordingly, the PSI tibial pin guide 10 includes one or more anchor elements disposed at different anchor points. In this case, at least three anchor elements are provided, namely the two bone spikes 14 which abut medially-laterally opposite sides of the tibial plateau P and the distally located jack screw 18. Importantly, each of these anchor elements is disposed at a location on the PSI tibial pin guide 10 which corresponds to, or more particularly overlies, point on the bone which correspond to areas of expected high accuracy on the X-ray generated bone model. More particularly, the two bone spikes 14 are located substantially along a proximal bone peripheral contour as defined in a frontal X-ray image taken of the tibia T, and the distal jack screw 18 is located substantially along an anterior bone peripheral contour as defined in a medial or a lateral X-ray image take of the tibia T.

The body 12 of the PSI tibial pin guide 10 also includes a pin guide element 22 disposed at a distal end of a portion of the body adjacent the distally extending portion 15. A pair of pin guide holes 24 extend through the pin guide element 22, and are configured to receive therethrough the bone pins 31 which are used to mount the resection cutting block 30 to the tibia (see FIG. 4).

The PSI tibial pin guide 10 also includes an optical positioning element which is used to position the PSI tibial pin guide 10 in the desired location relative to the tibia T. This optical positioning element includes a laser 26 which is engaged to a laser mount 27 disposed on an extension bar 25 protruding from the body 12 of the PSI tibial pin guide 10. The laser 26 produces a laser beam B, which may be either a point laser beam or a planar beam as shown in FIG. 2. The laser 26 is positioned such that its laser beam B projects onto the ankle and/or foot of the patient. By aligning the laser beam B with either anatomical landmarks on the foot (such as the malleoli of the ankle, for example) or other reference points or markings on another object substantially fixed relative to the ankle (such as the ankle boot 40 as shown in FIG. 5, for example), the user can position the PSI tibial pin guide 10, and therefore the pin guide holes 24 of the pin guide element 22 in a predetermined location which will result in the pins 31, when inserted through the pin guide holes 24 and fastened into the bone, to position the resection cutting block 30 mounted to these pins 31 in a selected position and orientation to perform the proximal resection cut of the tibia.

Figure 5:
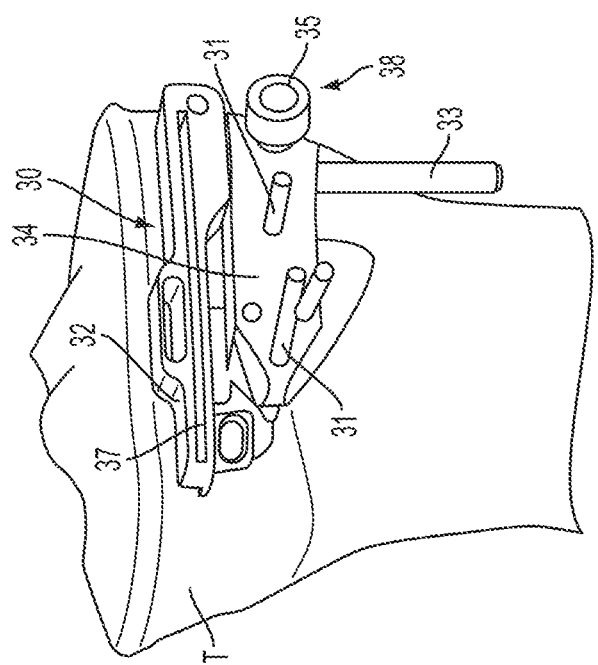
FIG. 5 is a top perspective view of a Flexion-Extension alignment boot used in conjunction with the PSI tibial pin guide of FIG. 2.

Referring more specifically to FIG. 5, the boot 40 may optionally be used in order to serve as a reference guide for aligning the PSI tibial pin guide 10 using the laser 26 as described above. More particularly, the boot 40 may include markings or other visually identifiable demarcations, with which the laser beam B of the laser 26 can be aligned, thereby providing additional guidance to the user as the correct alignment of the laser, and thus the PSI tibial pin guide 10 to which it is fixed, in the F-E direction.

Because the tibial pin guide 10 is a PSI component, it is designed and configured to tailor to the specific anatomical features of the tibia T to which it is intended to be mounted. Therefore, while each tibial pin guide 10 will be slightly different to accommodate particularities of each patient's bone, they nevertheless include one or more anchor points thereon that are adapted to abut and/or otherwise engage a surface of the tibia T and that are disposed at one or more locations of the PSI tibial pin guide 10 which correspond to areas of expected high accuracy on a digital bone model generated only by X-ray scans.

Referring now to FIG. 4 in more detail, a PSI tibial resection cut guide 30 of the present system is shown which including a cutting block 32 having a saw slot 37 extending therethrough and a base block 34 that is itself fastened in place on the tibia T using the cut guide pins 31. The pins 31 are positioned and fixed in place as described above using the PSI tibial pin guide 10. The cutting block 32 is adjustable in one or more directions relative to the base block 34, using a locking adjustment mechanism 38. In the embodiment as shown in FIG. 4, this locking adjustment mechanism 38 includes a stem 33 which forms part of the cutting block 32 and a mating opening in the base block 34 through which the stem extends. A locking screw 35 is used to fix the base block 34 to the stem 33 of the cutting block 33, such as to prevent relative movement therebetween when the screw is tightened. As the stem 33 can slide within the opening in the base block, the cutting block 32 can accordingly be displaced in a proximal-distal direction, in order to increase or decrease the depth of the proximal resection cut as required. Accordingly, once the pins 31 are in place, the base block 34 is slid onto the pins 31, whereupon the position of the cutting block 32 relative to the fixed base block 34 can be adjusted as required. Once the predetermined position for the cutting guide slot 37, and therefore the cutting block 32, is reached, the locking mechanism 38 is actuated to fix the cutting block 32 in the appropriate position.

Figure 6:
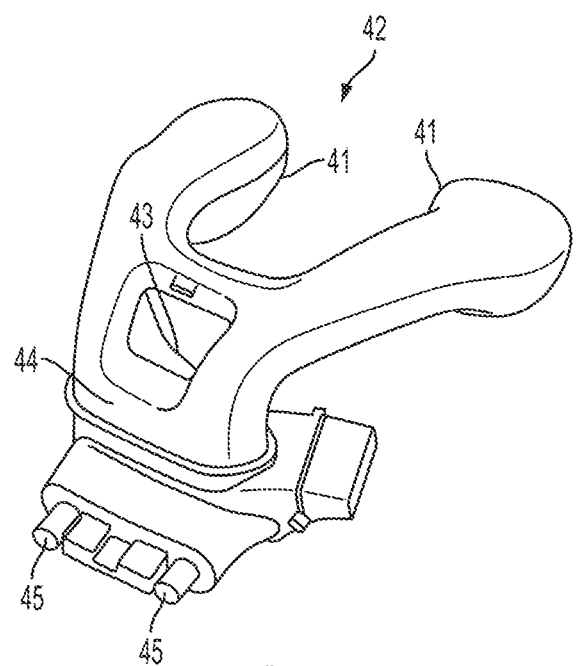
FIG. 6 is a perspective view of a PSI tibial pin guide jig in accordance with an alternate embodiment of the present disclosure.

FIG. 6 shows a PSI tibial pin guide jig 40 in accordance with an alternate embodiment of the present disclosure. This PSI jig 40 may be alternately used to align and position the mounting pins 31 for the PSI tibial resection cut guide 30, however provides less adjustment features. The PSI tibial guide jig 40 is more akin to pin placement jigs used in conjunction with MRI-generated digital bone models. Nonetheless, however, the PSI tibia pin guide jig 40 is specifically designed to be used with digital bone model generated only using X-ray images.

Accordingly, the PSI jig 40 also includes one or more anchor elements disposed at different anchor points, which in this embodiment includes two bone spikes 41 which abut medially-laterally opposite sides of the tibial plateau and an anterior abutting element 43 disposed on the distally extending body 44. A pair of pin holes 45 also extend through the body 44, and are used as described above to position the pins 31 used to mount the resection cutting block 30 to the tibia. Much as per the PSI tibial pin guide 10 described above, each of the anchor elements of the PSI jig 40 is disposed at a location on the PSI component which corresponds to, or more particularly overlies, a point on the bone which is disposed in areas of expected high accuracy on the X-ray generated digital bone model.

Figure 7:
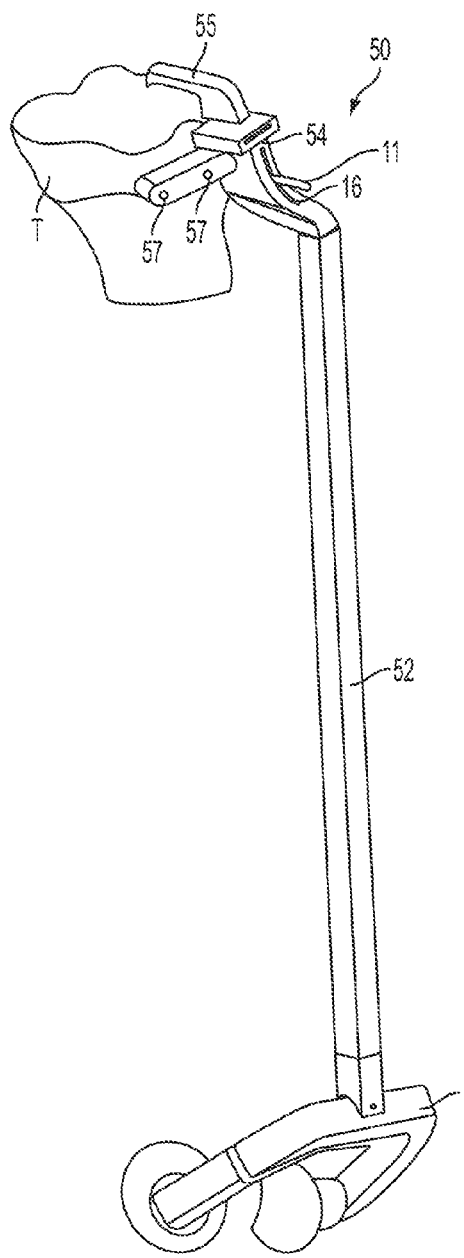
FIG. 7 is a perspective view of a PSI tibial extra-medullary guide in accordance with an embodiment of the present disclosure.
Figure 8:
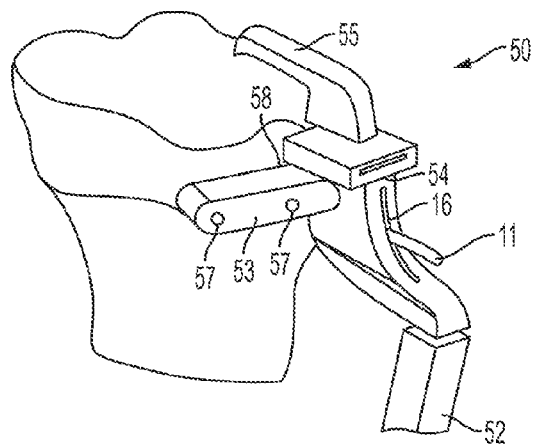
FIG. 8 is a partial perspective view of a proximal portion of the PSI tibial extra-medullary guide of FIG. 7.

Referring now to FIGS. 7-8, an alternate PSI component of the presently proposed suite of surgical implements is shown, which could alternately be used instead of the PSI tibial pin guide 10 or the PSI jig 40. In this embodiment, a PSI tibial extra-medullary (E-M) guide 50 (or simply "PSI E-M guide") is provided, which can be similarly used to accurately position the pins 31 to be used to mount the resection cutting guide 30 to the proximal end of the tibia T. The PSI E-M guide 50 differs from the previously described pin guides in that it includes an elongated rigid alignment rod 52 which extends distally from the upper mounting body 54, and which has a malleoli clamping element 56 at its distal end. While the alignment rod 52 may be standardized across all, or at least a number of patient sub-populations, each of the opposed end portions, namely the proximal mounting body 54 and the distal malleoli clamping element 56, is a PSI component that is purposed designed based on the anatomical features and needs of the individual patient. One of the possible benefits of the PSI E-M guide 50 is that it permits a less invasive surgical procedure (i.e. minimally invasive surgery), because no arms having spikes are included for contact with the tibial plateau. Accordingly, less of the bone needs to be accessed for engagement of the PSI E-M guide 50 thereto.

Much as per the PSI tibial pin guide 10 described above, however, the PSI E-M guide 50 is first located relative to the tibia T by an anterior pin 11 which mates within a corresponding slot 16 formed, in this case, in the proximal body 54 of the PSI E-M guide 50. This pin-slot engagement between the anterior pin 11 and the proximal body 54 of the PSI E-M guide 50 sets, or constrains, the rotation of the device. The proximal body 54 also includes a posteriorly extending finger 55 which includes a visual guide, such as an arrow marking or shape for example, which can be aligned with a known mechanical axis entry point on the tibia T so permit for the verification of the alignment with the mechanical axis of the tibia, thereby permitting the V-V alignment of the of the PSI E-M guide 50.

A posterior abutting element 58 is disposed behind the proximal body 54 of the PSI E-M guide 50, and provides an anchor element which abuts the anterior surface of the tibia T for positioning the component relative thereto. This abutting anchor element 58 is accordingly disposed at a location on the PSI component which corresponds to a point on the bone which is disposed in an area of expected high accuracy on the X-ray generated digital bone model (namely, along the anterior peripheral contour of the proximal tibia). The proximal body also includes a medially extending portion 53 having two pin holes 57 extending therethrough for receiving, and thus positioning, the pins 31 used to mount the resection cutting guide 30 thereto.

Although the relative orientation of the pins 31 can be varied somewhat when using the PSI E-M guide 50, it is otherwise not readily adjustable (e.g. in height, etc). Rather, because both the distal malleoli clamp 56 and the proximal body 54 are both PSI components purposed design for the individual bone, the PSI E-M guide 50 can be designed such as to be accurately mounted to the tibia T to allow the pins 31 to be inserted through the guide holes 57 in their determined position and orientation.

Figure 10:
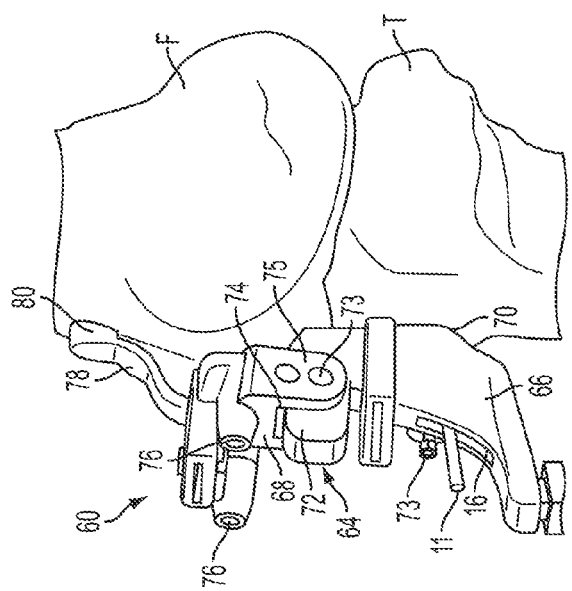
FIG. 10 is a partial perspective view of a proximal portion of the PSI HKA instrument of FIG. 9.
Figure 9:
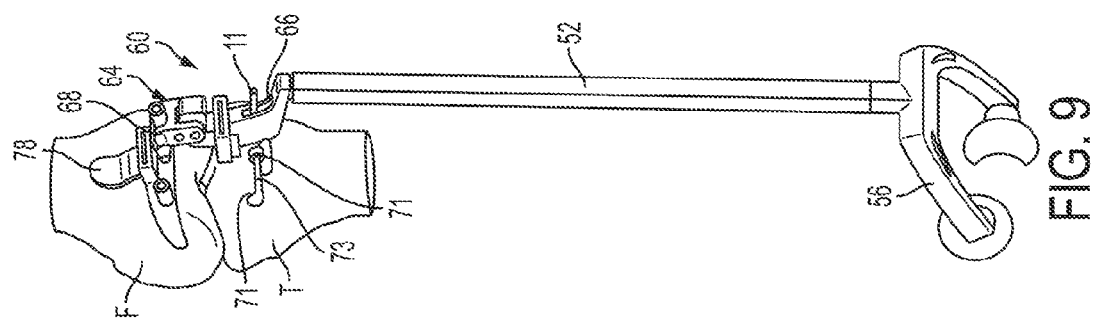
FIG. 9 is a perspective view of a tibia mounted PSI hip knee angle (HKA) instrument having a malleoli clamp, in accordance with an embodiment of the present disclosure.

Referring now to FIGS. 9-10, another alternate PSI component of the presently proposed suite of surgical implements is shown, which could alternately be used instead of the PSI tibial pin guide 10, the PSI jig 40 or the PSI E-M guide 50. In this embodiment, a PSI hip-knee-ankle (HKA) instrument 60 is provided, which can be similarly used to accurately position the pins 31 to be used to mount the resection cutting guide 30 to the proximal end of the tibia T. The PSI HKA instrument 60 includes an elongated rigid alignment rod 52, of fixed length, which extends distally from an upper mounting body 64 and which has a malleoli clamping element 56 at its distal end, much as per the PSI E-M guide 50 described above. Accordingly, the PSI malleoli clamping element 56 is used to clamp the component onto the malleoli of the patient, thereby aligning the instrument with the mechanical axis of the tibia.

In contrast to the previously described instruments, however, the proximal end of PSI HKA instrument 60 engages both the tibia and the femur, as seen in FIGS. 9 and 10. More particularly, the PSI proximal mounting body 64 of the PSI HKA instrument 60 includes both a tibial portion 66 and a femoral portion 68.

The tibial portion 66 is engaged in place relative to the tibia using an anterior pin 11 which is received within a corresponding slot 16, in the same manner as described above with the previously tibial instruments. This pin-slot engagement between the anterior pin 11 and the slot 16 in the tibial portion 66 of the PSI proximal body 64 sets, or constrains, the rotation of the device.

A posterior abutting element 70 is disposed behind the tibial portion 66 of the PSI proximal body 64, and provides an anchor element which abuts the anterior surface of the tibia T for positioning the component relative thereto. This abutting anchor element 70 is accordingly disposed at a location on the PSI component which corresponds to a point on the tibia which is disposed in an area of expected high accuracy on the X-ray generated digital bone model (namely, along the anterior peripheral contour of the proximal tibia). The tibial portion 66 of the PSI proximal body 64 also includes a medially extending portion 73 having two pin holes 71 extending therethrough for receiving, and thus positioning, the pins 31 used to mount the resection cutting guide 30 to the tibia T.

The femoral portion 68 of the PSI proximal mounting body 64 of the PSI HKA instrument 60 is interconnected with the tibial portion 66 by a sliding and/or pivoting joint connection which allows for one or more of relative P-D and F-E displacement between the two portions 66 and 68, but does not allow for relative angular rotation therebetween. More particularly, the uppermost end of the tibial portion 66 forms a plate 72 which is received within a corresponding slot 74 formed in the lower end of the femoral portion 68. The slot 74 therefore defines two spaced apart flanges 75 between which the plate 72 is received. Two holes 73 are provided in each of the flanges 75, and two correspondingly sized holes (not visible) are also defined through the plate 72. These holes may be aligned, such that a pivot pin is fed therethrough. Accordingly, without any such pivot pin in place, this joint between the tibial and femoral portions 66 and 68 allows for relative sliding displacement therebetween, substantially in the proximal-distal direction. However, when a single pin is disposed through one of the pin holes 73 and the corresponding hole in the plate 72, a pivoting interconnection between the two portions 66, 68 is thereby formed. This accordingly allows for relative rotation therebetween in the flexion-extension plane. Further, if a second pin is disposed through the other of the two pin holes 73 and the corresponding hole in the plate 72, no further rotation is permitted between the tibial portion 66 and the femoral portion 68 of the PSI proximal mounting body 64. This adjustment mechanism therefore provides adjustment flexibility in order to be able to selectively displace (e.g. translate or rotate), or lock, the tibial portion 66 and the femoral portion 68 of the PSI body 64 with respect to each other.

The femoral portion 68 of the PSI proximal mounting body 64 also includes a pair of pin holes 76 which extend through the body thereof and receive pins 31 therethrough for mounting a resection cutting guide to the femur, once the PSI HKA instrument 60 is positioned in place. The resection cutting guide may be the same PSI resection cutting guide 30 as described above (see FIG. 4), or alternately a different one specific for the femur. In order to accurate locate the femoral portion 68 of the PSI proximal mounting body 64, it also includes a proximally extending blade 78 having a femur abutting anchor element 80 thereon. In the same manner as those previously describe above, the femur abutting anchor element 80 is also disposed at a location on the PSI component which corresponds to a point on the bone (in this case the femur) which is disposed in an area of expected high accuracy on the X-ray generated digital bone model (namely, in this case, along the anterior peripheral contour of the distal femur).

Figure 11:
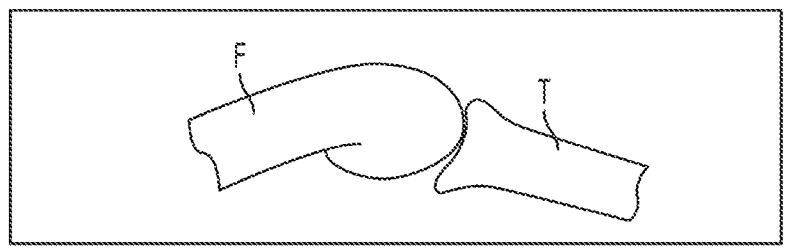
FIG. 11 is a schematic side elevation view of a leg alignment jig for use within the X-ray produced PSI tibial guides of the present disclosure, for use in performing TKR surgery.
Figure 11:
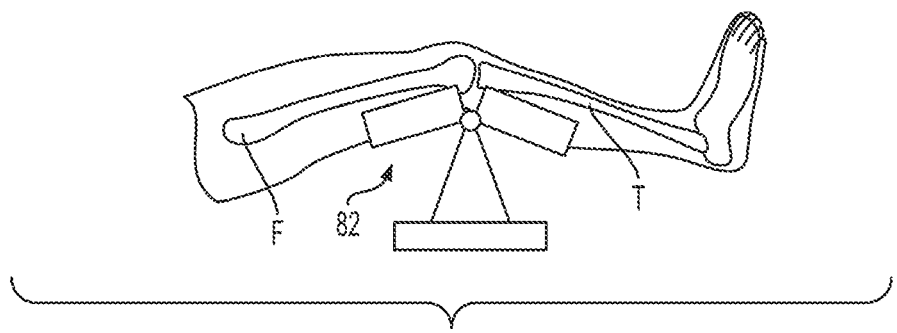

When using the PSI HKA instrument 60, the pins for the tibial resection are positioned, aligned and fixed in place in the same manner as per the PSI E-M guide 50 described above. However, in order to also correctly locate the PSI HKA instrument 60 to allow for pins for the femoral resection to be positioned in the desired position and orientation, both the tibia T and femur F are preferably positioned in the same relative orientation as when the X-ray scans were taken. Accordingly, in order to do so, a leg alignment jig 82 may be provided, as shown in FIG. 11. The leg alignment jig 82 is thus configured such as to position the leg of the patient, and thus the tibia T and femur F thereof, in a substantially identical relative position as when the X-ray scans were taken of the bones. The leg alignment jig 82 therefore allows the surgeon to set the leg as it was taken during the X-ray, thereby providing the best positioning for reproducing the planning and therefore maximizing precision of the operation. While the use of such a leg alignment jig 82 is not necessary, it may be useful to use this additional component for the reasons above.

Figure 14:
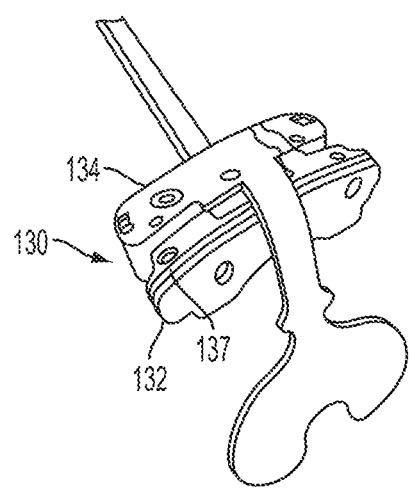
FIG. 14 is a perspective view of a femoral resection cut guide for use in conjunction with the PSI femoral pin guide of FIGS. 13a-13b.
Figure 15A:
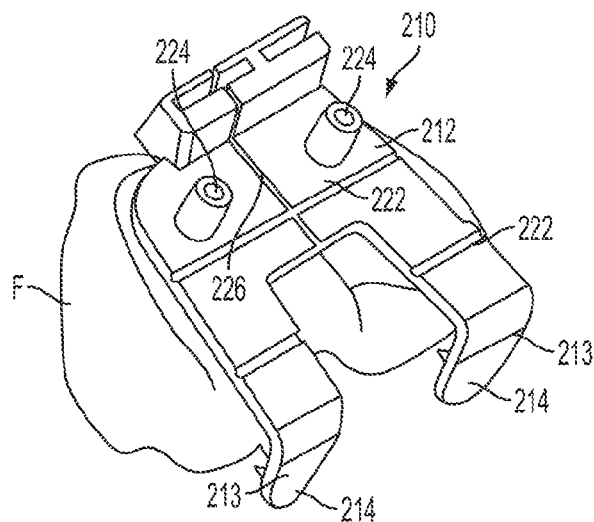
FIG. 15a is a distal perspective view of a PSI anterior-posterior (A-P) sizer in accordance with one embodiment of the present disclosure.
Figure 15B:
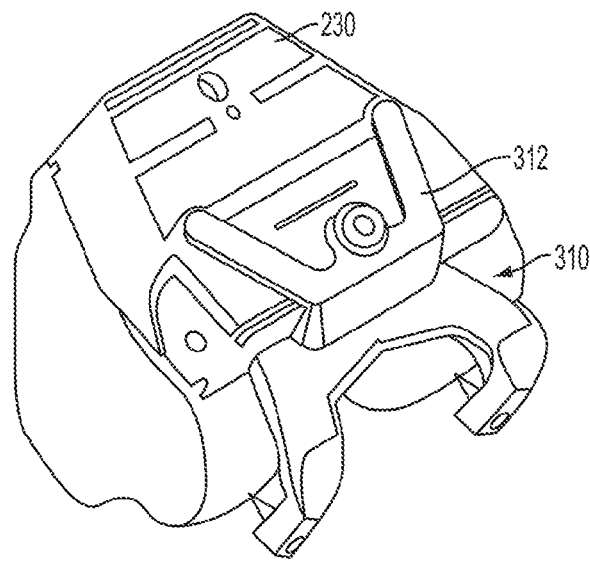
FIG. 15b is a distal perspective view of a PSI A-P sizer in accordance with an alternate embodiment of the present disclosure, shown positioning a posterior cutting guide thereon.

Given that the PSI HKA instrument 60 is also used to locate the pins for mounting to the femur, the PSI HKA instrument 60 can also be used in conjunction with the adjustable femoral resection cutting guide 130 of FIG. 14, and the PSI A-P sizers 210 and 310 of FIGS. 15*a* and 15*b*.

Figure 12:
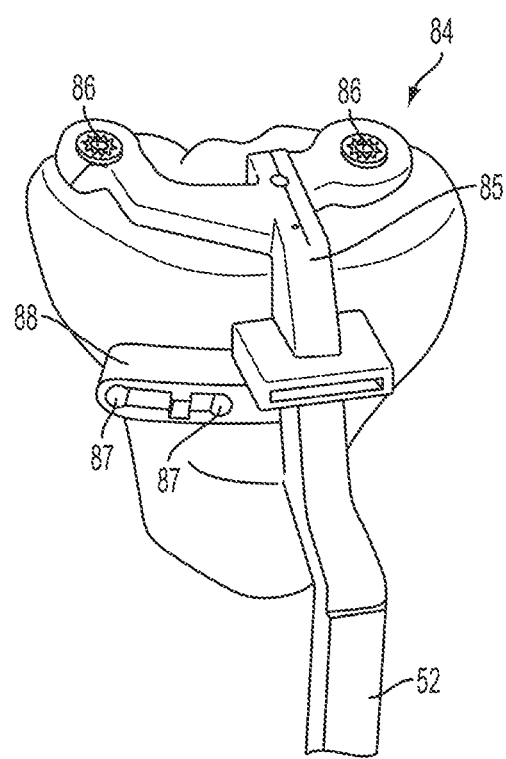
FIG. 12 is a partial perspective view of a proximal portion of a hybrid PSI tibial pin and extra-medullary guide in accordance with another embodiment of the present disclosure.

FIG. 12 depicts a final embodiment of a PSI tibial pin guide component, which is a hybrid PSI pin and E-M guide 84. Essentially, this embodiment is a combination of the PSI tibial pin guide 10 and the PSI E-M guide 50. However, the PSI pin and E-M guide 84 differs in that it does not use or require an anterior locating pin 11, as per the devices of the above-mentioned embodiments. Accordingly, the proximal mounting body 85 has bone spikes 86 which form proximal anchor elements that engage the tibial plateau, which set the V-V angular position of the PSI guide 84. Because these anchor elements 86 are offset from each other in the anterior-posterior direction, they also serve to set rotational position of the PSI guide 84. The distal malleoli ankle clamps (not shown in FIG. 12), located at the end of the alignment rod 52, are used to set the F-E position. As per the embodiments above, the proximal mounting body 85 also includes a medially extending portion 88 through which a pair of pin holes 87 extend, which are used to guide the pins 31 of the resection cutting guide block 30.

Femoral Components

Much as per the tibial components described above, the present suite of PSI implement for TKR surgery also include a number of embodiments of components which can be used for positioning the locating pins 31 on the femur, which used to mount a resection cutting block, such as the resection cutting guide 30 as described above (FIG. 4) which can also be used to resect the distal femur. Again, these PSI components are also specifically designed to be used when the digital bone model of the patient's femur is generated using only X-ray images.

Figure 13B:
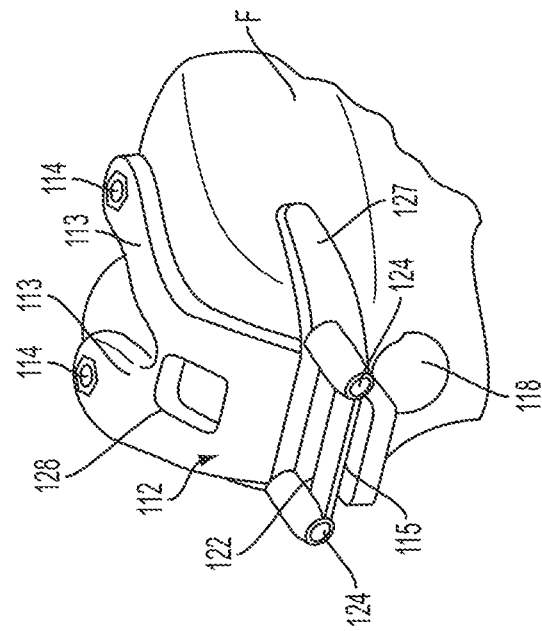
Figure 13A:
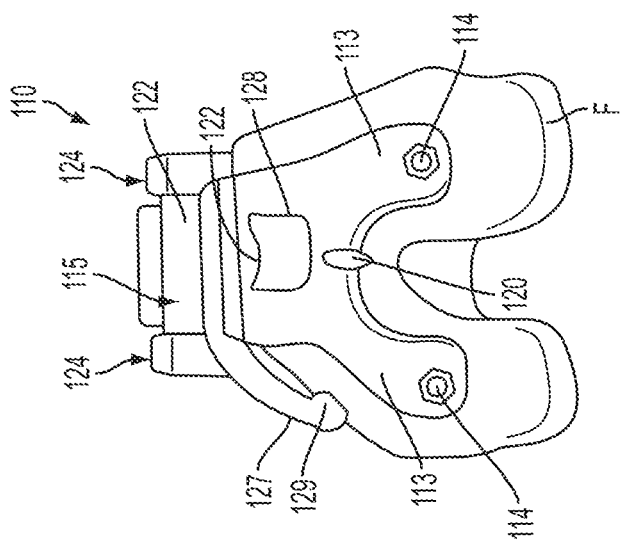
FIG. 13a is a distal end view of a PSI femoral pin guide, produced based on X-rays of the femur and for use in performing femoral resection during a TKR surgery.

Referring to FIGS. 13*a*-13*b*, a PSI femoral pin guide 110 is shown which adapted to be mounted to the distal femur and which is produced based on at least two X-rays of the femur, taken from two different angular positions. The PSI femoral pin guide 110 includes generally a body 112 including a proximally extending portion 115 and a pair of posteriorly extending arms 113. The posteriorly extending arms 113 each have a distal anchor element 114 disposed near the remote ends thereof, the two distal anchor elements 114 comprising bone spikes or nails which are adapted to piece any cartilage, if necessary, and abut directly on the distal condylar surfaces of the femur. These distal bone anchors 114 accordingly locate, or constrain, the PSI femoral pin guide 110 in the V-V orientation. The proximally extending portion 115 includes an anteriorly extending blade 118 which acts abuts the anterior surface of the distal femur and thus serves as another anchor element for locating the PSI guide 110. The anteriorly extending blade 118 provides constraint in the F-E orientation.

Accordingly, the PSI femoral pin guide 110 includes one or more anchor elements disposed at different anchor points. In this case, at least three anchor elements are provided, namely the two distal bone spikes 114 which abut medially-laterally opposite sides of the distal condylar surfaces and anteriorly extending blade 118. Each of these anchor elements is disposed at a location on the PSI femoral pin guide 110 which corresponds to, or more particularly overlies, points on the bone which correspond to areas of expected high accuracy on the X-ray generated bone model. More particularly, the two distal bone spikes 114 are located substantially along a distal bone peripheral contour as defined in a frontal X-ray image taken of the femur F, and the anteriorly extending blade 118 is located substantially along an anterior bone peripheral contour as defined in a medial or a lateral X-ray image take of the femur F.

The body 112 of the PSI femoral pin guide 110 also includes a pin guide element 122 disposed in the proximally extending portion 115 of the body 112. A pair of pin guide holes 124 extend through the pin guide element 122, and are configured to receive therethrough the bone pins 31 which are used to mount the resection cutting block 30 to the femur.

The PSI femoral pin guide 110 may also include one or more visual alignment guides, including for example an alignment arrow 120 which may be used to visually align the guide 110 with a known anatomical landmark and a patient-specific shaped contour 122 (see FIG. 13*a*) which is formed on an interior surface of the guide 110 and is visible though the window opening 128 defined in the body 112. The PSI contour 122 is specifically formed such as to correspond to the determined contour of the patient's bone on the anterior side of the distal femur, so that the surgeon can align this PSI contour 122 with the corresponding shape of the bone contour, thereby ensuring accurate alignment. Either of these visual alignment guides 122 and 128 may be used in order to align the PSI femoral pin guide 110 as required on the femur F.

The body 112 of the PSI femoral pin guide 110 may also include a medially extending arm 127 having a bone abutting element 129 at the end thereof, however this portion of the femur may be less accurately reproduced in the X-ray generated bone model, and therefore the medially extending arm 130 may be used for additional alignment guidance rather than primary location.

The PSI femoral pin guide 110 is designed to be used in conjunction with the adjustable femoral resection cutting guide 130 of FIG. 14, and the PSI A-P sizers 210 and 310 of FIGS. 15*a* and 15*b*, as will be seen.

FIG. 14 depicts an adjustable femoral resection cutting guide 130 which functions much like the resection cutting guide 30 as described above (FIG. 4) with reference to the tibial resection. The femoral resection cutting guide 130 is particularly adapted to be used in conjunction with the PSI femoral pin guide 110, which locates the pins in the femur to which the femoral resection cutting guide 130 is mounted. Similarly to the cutting guide 30, the femoral resection cutting guide 130 is also adjustable such that the portion 132 having the cutting guide slot 137 therein can be adjusted in the proximal-distal direction relative to the fixed mounting base 134 so as to be able to adjust at least a resection depth.

Referring now to FIG. 15a, a PSI anterior-posterior (A-P) sizer is mounted to the distal end of the femur, and may be used in conjunction with both the PSI femoral pin guide 110 and the femoral resection cutting guide 130 as described above.

The PSI A-P sizer 210 includes a, which sets the rotational position relative to the femur F based on the posterior condyles by employing two bone anchors in the form of bone spikes The PSI A-P sizer 210 includes generally a body 212 which abuts the distal end of the condyles of the femur F, and includes a pair of proximally extending arms 213. The posteriorly extending arms 213 each have a distal anchor element 214 disposed near the remote ends thereof, the two distal anchor elements 214 comprising bone spikes or nails which are adapted to piece any cartilage, if necessary, and abut directly on the posterior condylar surfaces of the distal femur. These bone anchors 114 accordingly set, or constrain, the PSI A-P sizer 210 in rotation.

Accordingly, the PSI A-P sizer 210 includes one or more anchor elements disposed at different anchor points. In this case, at least two anchor elements are provided, namely the two bone spikes 214 which abut posterior condyles. Each of these anchor elements is disposed at a location on the PSI A-P sizer 210 which corresponds to, or more particularly overlies, points on the bone which correspond to areas of expected high accuracy on the X-ray generated bone model. More particularly, the two bone spikes 214 are located substantially along a posterior bone peripheral contour as defined in a medial or lateral side X-ray image taken of the femur F.

The body 212 of the PSI A-P sizer 210 also includes a pin guide element 222 of the body 212. A pair of pin guide holes 224 extend through the pin guide element 222, and are configured to receive therethrough the bone pins which mount a posterior resection cutting block, such as the "4-in-1" cutting guide block 230 as shown in FIG. 15b, to the femur in order to perform the posterior resection cuts.

The PSI A-P sizer 210 may also include one or more visual alignment features, including for example the transverse marking lines 220 on the body 212 which define resection cut line positions and the central marking line 226 which defines the trans-epicondylar axis line.

In FIG. 15b, an alternate PSI A-P sizer 310 is shown, which is similar to the PSI A-P sizer 210 but having an additional attachment clip 312 for engaging the "4-in-1" posterior cutting guide block 230.

Figure 15C:
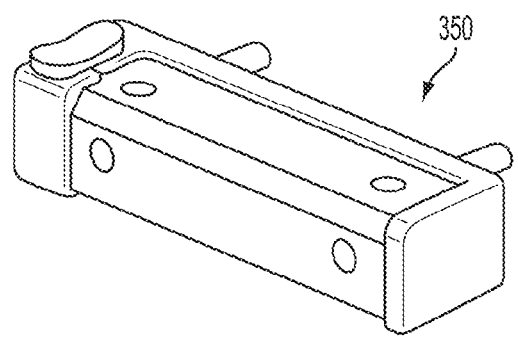
FIG. 15c is a perspective view of an additional instrument for us in re-positioning the posterior cutting guide shown in FIG. 15b.

FIG. 15c depicts simply an additional adjustment instrument 350 for use in re-positioning the posterior cutting guide block 230 relative to its mounting pins and thus relative to the bone. For example, the adjustment instrument 350 permit the sliding displacement of the posterior cutting guide block 230 in the anterior posterior direction and/or rotating the posterior cutting guide block 230 internally or externally.

Figure 16:
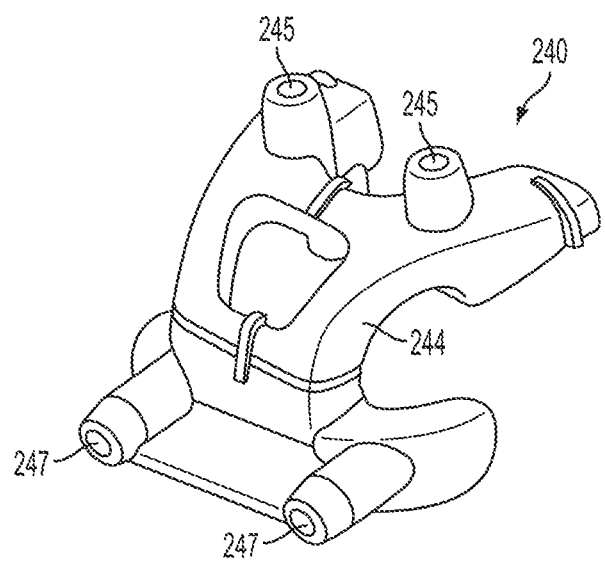
FIG. 16 is a perspective view of a PSI femoral pin guide jig in accordance with an alternate embodiment of the present disclosure.

FIG. 16 shows a PSI femoral pin guide jig 240 in accordance with an alternate embodiment of the present disclosure. Much as per the PSI tibial pin guide jig 40 of FIG. 6, the PSI femoral pin guide jig 240 may be alternately used to align and position the mounting pins for the femoral resection cut guides, however provides less adjustment features. The PSI femoral pin guide jig 240 is more akin to pin placement jigs used in conjunction with MRI-generated digital bone models. Nonetheless, however, the PSI femoral pin guide jig 240 is specifically designed to be used with digital bone model generated only using X-ray images. Accordingly, the PSI femoral pin guide jig 240 also includes one or more anchor elements disposed at different anchor points. Two different pairs of pin holes 245 and 247 also extend through the body 244, and are used as described above to position the pins used to mount the resection cutting block to the femur. The anchor elements of the PSI femoral pin guide jig 240 which abut the femur are disposed at locations on the PSI component which correspond to, or more particularly overly, points on the bone which are disposed in areas of expected high accuracy on the X-ray generated digital bone model.

The embodiments of the invention described herein are intended to be exemplary. Those skilled in the art will therefore appreciate that the present description is illustrative only, and that various alternatives and modifications can be devised without departing from the scope of the present invention.

Accordingly, the present description is intended to embrace all such alternatives, modifications and variances.

The invention claimed is:

1. A method of creating a patient specific instrument for use in knee replacement surgery, the method comprising:
   performing at least two two-dimensional X-ray scans of one or more bones, each of the two-dimensional X-ray scans being taken from different angular positions, the different angular positions being substantially perpendicular to each other;
   generating a digital bone model of said one or more bones based solely on the two-dimensional X-ray scans;
   planning the patient specific instrument based on the digital bone model, including determining locations for one or more anchor points on the patient specific instrument which are adapted to abut a surface of said one or more bones, the determined locations of the one or more anchor points being disposed on the patient specific instrument corresponding to areas of expected high accuracy on the digital bone model generated by the two-dimensional X-ray scans, said areas of expected high accuracy including at least a peripheral bone contour in at least one of said angular positions; and
   producing the patient specific instrument having said one or more anchor points thereon.

2. The method of claim 1, further comprising defining the areas of expected high accuracy to include at least a peripheral bone contour in at least one of the angular positions of the two-dimensional X-ray scans.

3. The method of claim 1, wherein the step of performing the at least two two-dimensional X-ray scans further comprises taking a first one of the two-dimensional X-ray scans from a frontal position and taking a second one of the two-dimensional X-rays scan from a medical or lateral position.

4. The method of claim 1, further comprising increasing the accuracy of the digital bone model by performing more than two two-dimensional X-rays scans, each from a different angular position.

5. The method of claim 1, further comprising using a computer assisted surgery system to perform the steps of generating the digital bone model and planning the patient specific instrument.

6. The method of claim 1, further comprising producing the patient specific instrument using an additive manufacturing process.

7. The method of claim 1, wherein the step of planning the patient specific instrument further comprises selecting the patient specific instrument to be a patient specific pin guide adapted for aligning bone pins on at least one of a tibia and a femur, the bone pins being operable to mount a resection cutting guide block.

8. The method of claim 7, further comprising providing the patient specific pin guide with a bone abutting anchor element for each of said one or more anchor points.

9. The method of claim 1, wherein the digital bone model of the one or more bones is based on only two two-dimensional X-ray scans.

* * * * *